(12) United States Patent
Clark et al.

(10) Patent No.: US 7,442,557 B1
(45) Date of Patent: Oct. 28, 2008

(54) BI-DIRECTIONAL FLOW ASSAY DEVICE WITH REAGENT BRIDGE

(75) Inventors: Scott Marshall Clark, Cape Elizabeth, ME (US); Michael Raymond Kepron, Standish, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 715 days.

(21) Appl. No.: 10/971,212

(22) Filed: Oct. 22, 2004

(51) Int. Cl.
*G01N 33/558* (2006.01)

(52) U.S. Cl. .................... 436/514; 422/55; 422/56; 422/58; 435/287.7; 435/810; 436/169; 436/808

(58) Field of Classification Search ............ 422/55, 422/57, 58, 56; 436/165, 169, 514, 518, 436/808, 170; 435/287.3, 287.6, 287.7, 287.9, 435/810, 7.1
See application file for complete search history.

(56) References Cited

U.S. PATENT DOCUMENTS

| | | | |
|---|---|---|---|
| 4,956,302 A | 9/1990 | Gordon et al. | |
| 5,217,905 A | 6/1993 | Marchand et al. | |
| 5,354,692 A | 10/1994 | Yang et al. | |
| 5,468,648 A | 11/1995 | Chandler | |
| 5,474,902 A | 12/1995 | Uylen et al. | |
| 5,569,608 A | 10/1996 | Sommer | |
| 5,602,040 A | 2/1997 | May et al. | |
| 5,604,110 A | 2/1997 | Baker et al. | |
| 5,607,863 A | 3/1997 | Chandler | |
| 5,622,871 A | 4/1997 | May et al. | |
| 5,624,809 A | 4/1997 | Skold et al. | |
| 5,648,274 A | 7/1997 | Chandler | |
| 5,654,162 A | 8/1997 | Guire et al. | |
| 5,698,395 A | 12/1997 | Ritterband et al. | |
| 5,726,010 A * | 3/1998 | Clark | 435/5 |
| 5,726,013 A * | 3/1998 | Clark | 435/5 |
| 5,744,096 A * | 4/1998 | Jones et al. | 422/58 |
| 5,750,333 A * | 5/1998 | Clark | 435/5 |
| 5,846,838 A | 12/1998 | Chandler | |
| 5,869,345 A | 2/1999 | Chandler | |
| 5,877,028 A | 3/1999 | Chandler et al. | |
| 5,879,951 A | 3/1999 | Sy | |
| 5,939,331 A | 8/1999 | Burd et al. | |
| 5,952,173 A | 9/1999 | Hansmann et al. | |
| 5,965,458 A | 10/1999 | Kouvonen et al. | |
| 6,007,999 A | 12/1999 | Clark | |
| 6,008,059 A | 12/1999 | Schrier et al. | |
| 6,020,147 A | 2/2000 | Guire et al. | |
| 6,136,549 A | 10/2000 | Feistel | |
| 6,140,136 A | 10/2000 | Lee | |
| 6,171,870 B1 | 1/2001 | Freitag | |
| 6,180,417 B1 | 1/2001 | Hajizadeh et al. | |
| 6,183,972 B1 | 2/2001 | Kuo et al. | |
| 6,194,224 B1 | 2/2001 | Good et al. | |

(Continued)

*Primary Examiner*—Duane Smith
*Assistant Examiner*—Robert A Clemente
(74) *Attorney, Agent, or Firm*—McDonnell Boehnen Hulbert & Berghoff LLP

(57) ABSTRACT

A device for conducting an assay to determine the presence or amount of an analyte in a fluid sample. The device includes a flow path that facilitates fluidic flow by capillary action. The flow path has a first fluid permeable region, a second fluid permeable region, a barrier that inhibits fluidic flow between the first and second regions, and a fluidic bridge. The bridge includes a fluid permeable material overlapping at least a portion of each of the first region, the barrier and the second region.

28 Claims, 1 Drawing Sheet

U.S. PATENT DOCUMENTS

| | | |
|---|---|---|
| 6,218,134 B1 | 4/2001 | Yamauchi et al. |
| 6,221,625 B1 | 4/2001 | Ashihara et al. |
| 6,228,660 B1 | 5/2001 | May et al. |
| 6,271,045 B1 | 8/2001 | Douglas et al. |
| 6,277,650 B1 | 8/2001 | Nazarah et al. |
| 6,287,875 B1 | 9/2001 | Geisberg |
| 6,306,642 B1 | 10/2001 | Nelson et al. |
| 6,365,417 B1 | 4/2002 | Fleming et al. |
| 6,472,226 B1 * | 10/2002 | Barradine et al. ............ 436/518 |
| 6,534,324 B1 | 3/2003 | Zin |
| 6,551,842 B1 | 4/2003 | Carpenter |
| 6,875,185 B2 * | 4/2005 | Wong et al. .................. 600/584 |
| 7,238,519 B2 * | 7/2007 | Bellet et al. ............... 435/287.2 |
| 7,279,136 B2 * | 10/2007 | Takeuchi et al. ............ 422/100 |

* cited by examiner

BI-DIRECTIONAL FLOW ASSAY DEVICE WITH REAGENT BRIDGE

FIELD OF THE INVENTION

The invention relates to lateral flow devices for performing specific binding assays.

BACKGROUND OF THE INVENTION

Lateral flow type devices for the detection and quantification of an analyte of interest in a fluid sample are well known. For example, such devices are described in U.S. Pat. Nos. 3,799,742; 3,811,840; 3,645,687; 4,435,504; 4,094,647; 3,246,339; 4,366,241; 3,888,629, and 5,750,333, each of which is incorporated by reference herein in its entirety. Generally, the devices comprise a solid phase fluid permeable flow path having immobilized thereon various capture reagents for the analyte (or analogue thereof) or conjugates involving binding partners for the analyte and members of signal producing systems (e.g., a label). The various assay formats used with these devices are well known for the direct or indirect detection of the analyte of interest in the test sample.

Numerous materials are known for the solid phase flow paths of the lateral flow devices. These materials are generally selected to have a low affinity for sample materials and other specific binding reagents, the ability to transport liquid by capillary action over a distance with consistent liquid flow across the flow path, and ready binding to immobilized specific binding reagents. The material chosen for a solid phase flow path partially controls the speed of fluid flow through the flow path. Flow speed is one of the variables that affect the sensitivity of the assay. If the sample flows too fast past the capture reagents immobilized on the flow path, specific binding reactions may not have enough time to occur, thus reducing the sensitivity of the assay. On the other hand, when liquid flows too slowly, the total time to complete the assay increases. This may be undesirable since the speed of the assay is an important feature for the consumer.

Balancing assay sensitivity with assay time provides a challenge since a single material may not provide all of the desired characteristics for the solid phase fluid flow path. Those materials that do provide such characteristics may be difficult and expensive to manufacture. Thus, what is needed is a convenient and cost effective method of balancing the total assay time with the sensitivity of the assay, while allowing easy manufacturability of the device.

SUMMARY OF THE INVENTION

In one aspect, the invention is directed to a device for conducting an assay to determine the presence or amount of an analyte in a fluid sample. The device includes a flow path that facilitates fluidic flow by capillary action. The flow path has a first fluid permeable region for sample entry, a second fluid permeable region, a substantially fluid impermeable barrier between the first and second regions, and a fluidic bridge. The bridge includes a fluid permeable material overlapping at least a portion of each of the first region, the barrier and the second region. The bridge provides fluid communication between the first and second regions and includes a detection zone having an immobilized capture reagent.

In another aspect, the invention is directed to a device for conducting an assay to determine the presence or amount of an analyte in a fluid sample. The device includes a flow path that facilitates fluidic flow by capillary action. The flow path includes a single piece of matrix material having a first fluid permeable region for sample entry; a second fluid permeable region; and a barrier that interrupts fluid communication between the first and second regions. The barrier is an area of the matrix material that has been treated to render the area substantially impermeable to liquid. The device also includes a fluidic bridge that includes a fluid permeable material overlapping at least a portion of each of the barrier, the first region, and the second region. The bridge provides fluid communication between the first and second regions.

In a further aspect, the invention is directed a method for producing a device for conducting an assay to determine the presence or amount of an analyte in a fluid sample. The device includes a flow path that facilitates fluidic flow by capillary action. The method includes providing a single piece of fluid permeable matrix material and creating a fluid impermeable barrier on the matrix material between a first region and a second region by treating the area with a substance to render the area substantially impermeable to fluid. The method also includes securing a fluidic bridge including a fluid permeable material to the matrix material so that the bridge overlaps at least a portion of each of the first region, the barrier and the second region.

In yet another aspect, the invention is directed to a device for conducting an assay to determine the presence or amount of an analyte in a fluid sample. The device includes a flow path that facilitates fluidic flow by capillary action. The flow path includes a single piece of hydrophobic matrix material that has been treated to have at least two fluid permeable regions separated by an untreated region that acts as a fluidic barrier between the at least two fluid permeable regions. A fluidic bridge having a fluid permeable material overlaps at least a portion of each of the at least two fluid permeable regions and the untreated region so that the bridge provides fluid communication between the at least two fluid permeable regions.

DETAILED DESCRIPTION OF THE INVENTION

Figure 1:
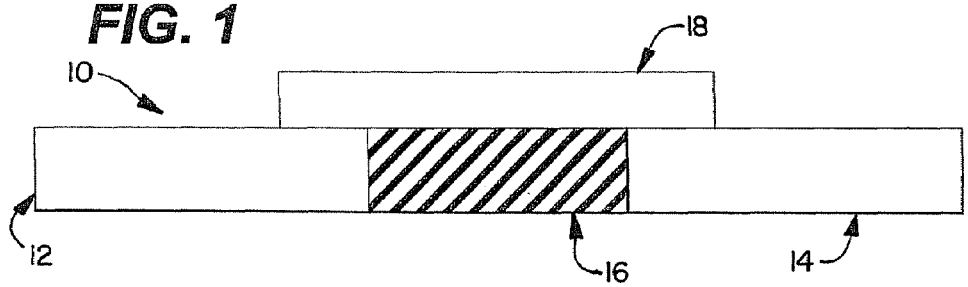
FIG. 1 is a cross sectional view of a fluid flow path matrix for use in the device of the present invention.

The present invention provides a device for conducting specific binding-pair assays that utilize capillarity-mediated, chromatographic transport, for the qualitative or quantitative analysis of selected analytes in samples. The invention is useful for a wide variety of assays, both ligand-based and non-ligand-based. Applicable ligand-based methodologies may include, but are not limited to, competitive immunoassays, non-competitive or so-called sandwich technique immunoassays, and blocking assays. The use of the invention is not limited to any particular analyte. The embodiments described herein are solely for illustrative purposes but are not intended to limit the scope of the invention to any particular set of binding partners or assay format.

Before describing the present invention in further detail, a number of terms will be defined. As used herein, the singular forms "a," "an," and "the" include plural referents unless the context clearly dictates otherwise.

By "analyte" is meant a molecule or substance to be detected. For example, an analyte, as used herein, may be a ligand, which is mono- or polyepitopic, antigenic or haptenic; it may be a single compound or plurality of compounds that share at least one common epitopic site; it may also be a receptor or an antibody.

An "analyte analog" is a specific derivative of the target analyte that may be optionally attached, either covalently or non-covalently, to other chemical species (e.g., a label). The analyte analog may be used, for example, to compete with the analogous target analyte for binding to the specific binding partner (i.e., competition assay). Where the modification of the analyte provides means to join the analyte analog to another molecule, or where the analyte has a functionality that is used to bind directly to another molecule, the analyte portion of the conjugate will be referred to as an analyte analog.

A "specific binding partner" or "binding partner" is a molecule, such as a receptor, binding protein, antibody or antibody fragment, or enzyme (which binds to its substrate), that possesses the ability to interact with another molecule in a highly specific polar and spatial manner.

An "antibody" is an immunoglobulin, or a derivative or fragment thereof, that is capable of specifically binding to an antigen in a receptor-ligand based reaction. The antibody or fragment may be polyclonal or monoclonal, or native or chimeric.

A "label" is any molecule that is bound (via covalent or non-covalent means, alone or encapsulated) to another molecule or solid support and that is chosen for specific characteristics that allow detection of the labeled molecule. Generally, labels are comprised of, but are not limited to, the following types: particulate metal and metal-derivatives, radioisotopes, catalytic or enzyme-based reactants, chromogenic substrates and chromophores, fluorescent and chemiluminescent molecules, and phosphors. The utilization of a label produces a signal that may be detected by means such as detection of electromagnetic radiation or direct visualization, and that can optionally be measured.

By "immobilized capture reagent" is meant a molecule that is bound covalently or non-covalently to a solid phase matrix or support and that has a specific affinity for an analyte of interest, analyte analogue, or other binding partners for the immobilized capture reagent. Preferably, the affinity arises by virtue of the immobilized reagent possessing a complementary three-dimensional structure to the analyte, analogue, or other binding partner. For example, as seen in the relationship between an enzyme and a substrate or an antigen and an antibody. Within a given pair including the analyte, either member may be considered to be the analyte or the capture reagent. The definition serves only to differentiate the members of the binding pair, i.e. the partner that is immobilized from the partner that is not immobilized.

A "labeled specific binding reagent" is a non-immobilized substance that specifically binds to the analyte (or analogue) and is bound, directly or indirectly, to a label.

In one aspect, the invention is directed to a device for performing an assay that determines the presence or quantity of an analyte in a fluid sample by capturing the analyte in a fluid flow path with at least one immobilized capture reagent in a detection zone on the fluid flow path. To facilitate detection, unbound material can be washed from the detection zone. The flow path of the device of the invention includes at least a fluid permeable first region, a fluid permeable second region, a substantially fluid impermeable barrier between the first and second regions, and a fluidic bridge that overlaps the barrier, at least a portion of the first region and at least a portion of the second region to provide fluid communication between the first and second regions. The bridge includes the detection zone with one or more immobilized capture reagent (s). The bridge, the barrier and the first and second sections are collectively referred to herein as the "flow path matrix."

The first and second fluid permeable regions together with the barrier may be one, two or three pieces of material, collectively referred to herein as a "barrier matrix" (i.e. the flow path matrix without the bridge). When the barrier matrix is a single piece of material, the barrier can be created by chemically treating a portion of the material between the first and second regions to render the portion substantially impermeable to fluids. The size of the portion treated is not critical as long as the treatment renders the portion substantially impermeable to fluid. When two or three pieces of material are used, the barrier may also include a space, which prohibits fluid communication between the first and second regions, with or without a hydrophobic spacer material. Further, the fluid path matrix may include two pieces of material where either the first or second region is on the same piece as the barrier and where the barrier portion of the material has been treated to render it fluid impermeable. In any of the matrices with two or three materials, the first and second regions may be the same or different materials.

The fluidic bridge is a fluid permeable material that may be the same or different than the material of the first and second regions of the flow path. The bridge is secured to the barrier matrix and the bridge overlaps the barrier, at least a portion of the first region and at least a portion of the second region. Thus, the fluidic bridge provides fluid communication between the first and second regions. Thus, when fluid is introduced into the first region, the barrier directs the fluid flow into the fluidic bridge so that fluid flow is then directed through the detection zone and into the second region.

When the barrier and either or both of the first and second regions of the fluid flow path are a single piece of material, the barrier may be created by treating a portion of the material with one or more substances that render a portion substantially impermeable to fluid. Such substances include, for example, a fluoro methacrylate polymer such as FLUOR-PEL™ (Cytonix Corporation, Beltsville, Md.) and acrylic latex. Other substances can be used as long as the substance does not interfere with the performance of the assay. Also, hydrophobic fluid path materials can be used that are treated to create strategically placed hydrophilic zones. For example, non-woven polyester or sintered polyethylene matrix materials are generally hydrophobic until treated to become more hydrophilic, such as with a surfactant or plasma treatment. In a particular example, non-woven polyester material can be dipped in a 1% Triton X-100 solution to create hydrophilic properties in the matrix.

The barrier should be substantially impermeable to fluid so that sample liquid is directed from the first region into the bridge. In one aspect, the substantially fluid impermeable barrier is completely fluid impermeable and directs all of sample liquid flow into the bridge. However, it is not necessary that the barrier completely prevent fluid flow. Hydrophobic materials, or materials that are treated to render them hydrophobic, can be used such that the materials inhibit or interrupt a substantial portion of fluid flow through the barrier and thus direct the substantial portion of the sample liquid into the bridge. A substantially fluid impermeable barrier will inhibit the fluid flow through the barrier so that the fluid flow over the bridge will be faster than the fluid flow through the barrier. This ensures that there is the capillary action required to draw enough sample liquid through the detection zone to provide an accurate assay result.

The fluidic bridge can be secured to the fluid path matrix by any known means that provides fluid communication between the first region, the bridge and the second region. For example, suitable means include heat-activated dry film adhesives or pressure-sensitive adhesives, or the fluid path matrix and the bridge can be held together in a cartridge or other rigid or semi-rigid body to prevent the matrix and the bridge from separating.

When the bridge is a different material than the first and second regions, it can provide different flow characteristic than the first and second regions. Thus, flow characteristics of the material in the detection zone may be different than the flow characteristics in the first and second regions of the flow path.

There are several advantages of a device having the fluidic bridge as a separate component secured to the barrier matrix. First, invention allows for the preparation of the barrier matrix (the first region, the barrier and the second region) as a generic component of the device regardless of the analyte to be detected. Thus, the fluidic bridge can be customized with various immobilized capture reagents in the detection zone depending on analyte to be detected and the format of the assay, while the barrier matrix may be the same for several assays. This design also facilitates the manufacture of the device and can reduce production costs. Also, the fluidic bridge having the immobilized capture reagents in a detection zone may be of a different material than the barrier matrix so that the capillary properties of the material in the detection zone can be different than the properties of the first and second regions. The differences in the materials allows for the optimization of the specific binding reactions involving the immobilized capture reagents, labeled binding reagents and/or detector reagents. Such enhancement of interactions can result in increased assay sensitivity.

In addition, variation in the fluid flow path materials allows for the adjustment of the time of the assay. For example, by making the pore size of the fluidic bridge material small by using materials with small particle radii, the flow rate can be reduced as the surface area increases. The slower flow rate in the fluidic bridge can enhance the sensitivity of the assay as described above. To reduce the total assay time, the pore size of the first and second regions can be made large so that the flow rate in those regions increases without compromising sensitivity of the assay. Thus, by controlling the flow rate by varying the pore size of the different regions of the flow path, the sensitivity and total assay time can be controlled.

Materials for the barrier matrix and the fluidic bridge may be, for example, synthetic or natural fibers, including glass or cellulose-based materials; thermoplastic polymers, such as polyethylene, polypropylene, or polyester; sintered structures composed of particulate materials, for example, glass or various thermoplastic polymers; or cast membrane films composed of nitrocellulose, nylon, polysulfone or the like. The materials may also include sintered, fine particles of polyethylene, commonly known as porous polyethylene. Particulate polyethylene composed of cross-linked or ultra high molecular weight polyethylene is preferable. Such materials are available, for example, from Porex Corporation (Fairbum, Ga.).

In one aspect of the invention, a detector reagent is provided to detect a labeled specific binding reagent captured in the detection zone. The detector reagent participates with the label to produce one or more measurable signals to indicate the presence or quantity of the analyte in the sample.

Figure 2:
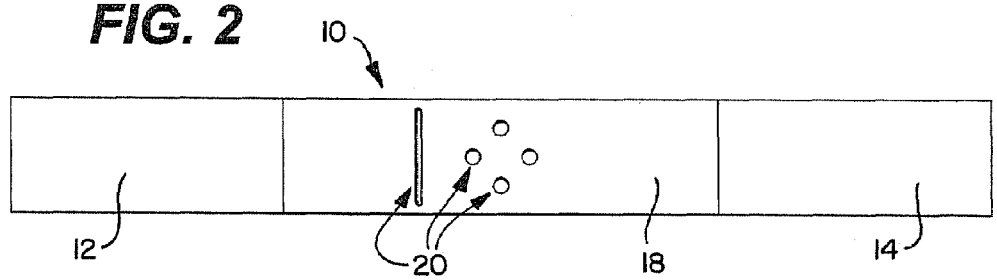
FIG. 2 is a top plan view of the fluid flow path matrix of FIG. 1.

FIGS. 1 and 2 provide an example of the fluid flow path of the device of the invention. A fluid flow path matrix 10 for use in the device of the invention is shown having a first fluid permeable region 12, a second fluid permeable region 14, and a barrier 16. A fluidic bridge 18 overlaps the first region 12, the second region 14, and the barrier 16 and is secured so that the bridge is in fluid communication with the first region and the second region. Immobilized capture reagents are shown in a detection zone 20 on the fluidic bridge in two formats, as a strip and as dots. Any format can be used, including various signals such as + or − signs, dashes, or any other format that can provide a visual signal to the operator. The barrier, the first region and the second region can be a single piece of matrix material, or it can be pieced together out of two or three pieces. The relative sizes of fluid permeable regions and the fluidic bridge can vary and the proportions depicted in the figures herein are for illustrative purposes only.

In another aspect of the invention, the device can be fashioned for a bi-directional capillary flow, that is, reversible flow, to transport an analyte from a fluid sample first in one direction and then in the opposite direction along the fluid flow path. Reversible flow facilitates elimination of unreacted sample and unbound reagent from the detection zone. The detector and/or a wash reagent flows along the assay device in the opposite direction to the original sample flow drawing with them unbound or unreacted constituents. Such reversible flow increases the sensitivity of the assay by removing unbound substances that contribute to non-specific binding reactions and background signals. Reversible flow assay devices are described, for example, in U.S. Pat. No. 5,750,333.

In another aspect, the device includes a wash and/or detector reagent in sealed container(s) and a means, for example a lance with a wick, for introducing the reagent(s) into the second region of the flow path, for example, by piercing the sealed containers. By "lance" is meant a component that is capable of piercing the seal of a liquid reagent container. Such a lance may also include a wick that facilitates flow of the liquid reagents out of their storage containers and into the flow path. By "wash reagent" is meant a liquid reagent that serves to remove unbound material from the detection zone having an immobilized capture reagent. By "detector reagent" is meant a liquid reagent that serves to both remove unbound material from the detection zone and to facilitate analyte detection. The detector reagent may contain a substrate, reactant, or any suitable reagent that, when brought in contact with the captured labeled specific binding reagent, produces a detectable reaction.

In another aspect of the invention, an absorbent reservoir is positioned, prior to use, so as not to contact the fluid flow path, and means are included in the device for moving the absorbent reservoir into fluidic contact with the flow path. In addition, the means for introducing the wash and detector reagents into the second region may be connected to the means for moving the absorbent reservoir into contact with the flow path matrix, allowing an operator to activate both mechanisms in a single operation.

Materials suitable for use as an absorbent reservoir are fibrous structures of natural and synthetic fibers such as cellulose and derivatized cellulose, for example, cellulose acetate. Such materials may have densities of about 0.1 to about 0.3 grams per cubic centimeter and void volume of about 60 to about 95 percent.

In another embodiment, the wash reagent is delivered before the detector reagent. This may be achieved by positioning the wash reagent entry port intermediate to the second region and the entry port for the detector reagent. This facilitates delivery of the wash reagent to the third region to facilitate removal of unbound sample and labeled specific binding reagent prior to delivery of the detector reagent. In addition, the means of delivering the detector reagent is connected to the means of delivering the wash reagent, for example, lances positioned and adapted to pierce both containers, so that an operator may apply both reagents in a single mechanical operation.

A reversible flow technique facilitates assays that are of low background and high specificity. In addition, the semi-automated nature of the assay devices and methods of the invention significantly reduces the level of technical sophistication required of an individual performing the binding assays described herein, facilitating assays that may be carried out in an environment remote from a laboratory and by practitioners with limited training.

The overall sequencing of the steps of the devices and methods of the invention are controlled by the flow of the liquids within the fluid flow path and the physical positioning of the sample and liquid reagent entry points relative to the position of the immobilized capturing reagent. Operator involvement is, in general, limited to a maximum of two steps: application of the sample and a one-step release of stored liquid reagents (wash and detector) that also mechanically contacts the absorbent reservoir with the flow path matrix.

Any or all of the above embodiments of the invention may be provided as a kit. In one particular example, such a kit would include a device of the invention complete with specific binding reagents, for example, non-immobilized labeled specific analyte binding reagents and immobilized capture reagents, as well as wash reagent and detector reagent. Positive and negative control reagents may also be included, if desired or appropriate. In addition, other additives may be included, such as stabilizers, buffers, and the like. The relative amounts of the various reagents may be varied widely, to provide for concentrations in solution of the reagents that substantially optimize the sensitivity of the assay. Particularly, the reagents may be provided as dry powders, usually lyophilized, which on dissolution will provide for a reagent solution having the appropriate concentrations for combining with the sample.

Figure 3:
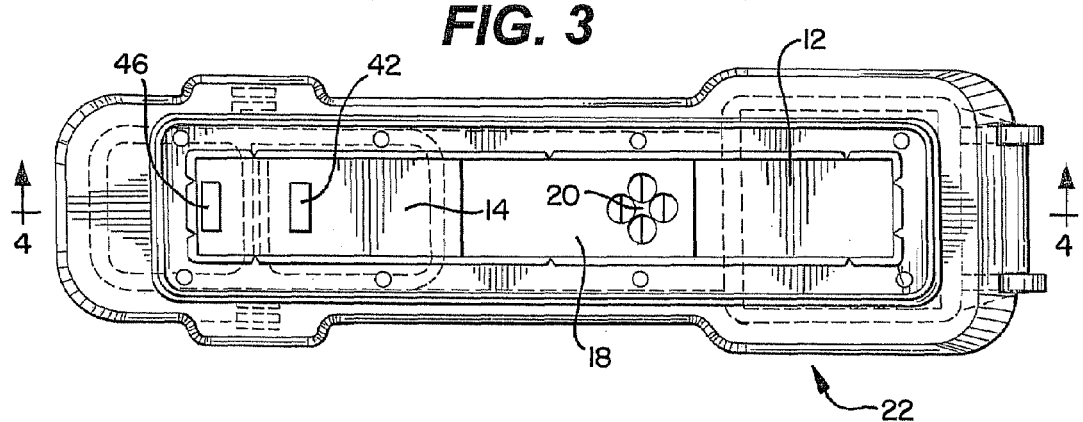
FIG. 3 is a top plan view of a device for carrying out a reversible flow chromatographic binding assay of the present invention.
Figure 4:
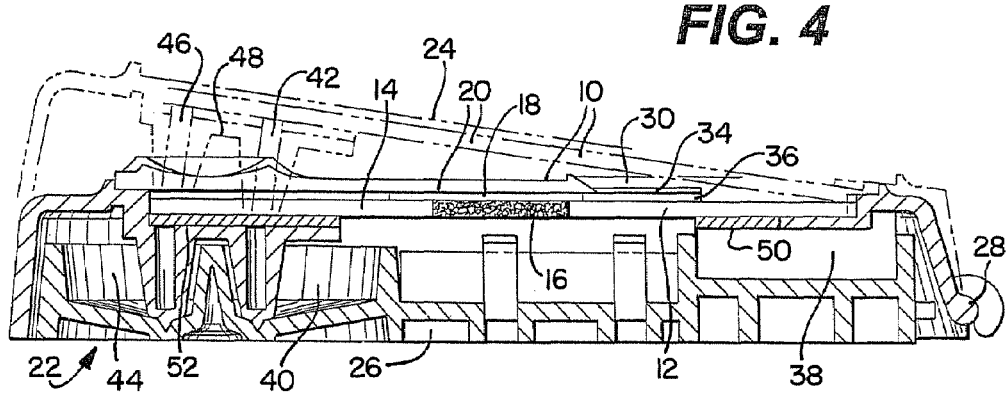
FIG. 4 is a cross sectional illustration of the device of FIG. 3. The top portion of the device housing is shown both as it is positioned prior to operator activation (in phantom) and as it is positioned after operator activation (solid lines).

FIGS. 3 and 4 depict one example of a device 22 according to the invention. Components of the device are enclosed within an upper housing portion 24 and a lower housing portion 26, pivotably disposed with respect to each other by means of a hinge 28. Such a housing serves to properly hold the components in place and to allow delivery of a sample to the fluid flow path 10 as well as to allow an operator to visually monitor assay results. The pivotal connection initially holds the two portions of the housing apart (allowing "forward" flow). Operator activation is accomplished by squeezing components 24 and 26 together, contacting the flow matrix with the absorbent reservoir and releasing the liquid reagents (as described below), enabling "reverse flow".

To carry out a binding assay using such a device, fluid sample is applied through a sample entry cup 30. The fluid sample is drawn into the flow matrix 10 as follows. First, the sample flows through a sample prefilter pad 34 that removes interfering particulate matter and, next, through a labeled specific binding reagent pad 36 upon which labeled specific binding reagent has been deposited and dried. Contact of the labeled specific binding reagent pad with the fluid sample results in dissolution of the labeled specific binding reagent into the sample, allowing sample analyte to bind to the labeled specific binding reagent; positioning of the labeled specific binding reagent pad adjacent to the sample entry cup increases the quantity of sample that contacts the dried reagent. In the alternative, the labeled specific binding reagent can be added to the sample before the sample is added to the device.

Sample and labeled specific binding reagent are then drawn, by capillary action, into the first region 12 of flow matrix 10 and transported in the "forward" direction towards the barrier 16 that directs fluid flow into the fluidic bridge 18 and towards and past the detection zone 20 where immobilized capture reagent has been incorporated into the fluidic bridge. At the detection zone 20, all binding species are present (i.e., sample, labeled specific binding reagent and immobilized capture reagent). Fluid flow continues in the forward direction and into the second region 14 until the fluid front reaches a desired position on the flow matrix (such as reaching an opening in upper housing portion 24, preferably located before the fluid reaches the region where wash reagent (described, below) is delivered to the flow matrix). At this time, housing components 24 and 26 are squeezed together by the operator (as described above), bringing the first region 12 of flow matrix 10 into contact with the absorbent reservoir 38. The absorbent reservoir is positioned toward one end of matrix 10 so as to draw the fluid out of the matrix and to reverse the direction of fluid flow within the device.

Upon flow reversal, liquid reagents are delivered to the flow matrix. In the device illustrated in FIGS. 3 and 4, such liquid reagents include a wash reagent and a detector reagent. The wash reagent is stored in a wash reagent storage vessel 40 and is delivered, by the wash reagent delivery wick 42 into the second region 14 of the flow matrix 10. The purpose of the wash reagent is to transport unbound sample and unbound labeled specific binding reagent along the flow matrix 10 and away from the detection zone 20. When the liquid flow in the device is reversed, the substantially fluid impermeable barrier directs all or a substantial portion the wash and detector reagents from the second region into the bridge.

Detector reagent is stored in the detector reagent storage vessel 44 and is delivered, by the detector reagent delivery wick 46 into second region 14 of the flow matrix 10. The detector reagent facilitates analyte detection. The device depicted in FIGS. 3 and 4 illustrates a physical linkage of the delivery wicks within the lance 48 that serves to both pierce the storage vessels and deliver the reagent to the flow matrix. This linkage facilitates the release of the two stored liquid reagents with a single action. Sequential utilization of the two reagents, i.e., wash reagent followed by detector reagent is accomplished by delivering the wash reagent closer to the absorbent reservoir 38 than the detector reagent. Fluid flow toward the absorbent reservoir causes the wash reagent to be pulled into the flow matrix 10 by capillary force. Once the volume of the delivered reagent has been absorbed into the flow matrix, displacing unbound sample and unbound labeled specific binding reagent, detector reagent is delivered into the flow matrix 10 by capillary force. Detector reagent displaces the wash reagent in the direction of the absorbent reservoir 38. When the detector reagent flows into the detection zone 20, complex formation is detectable, and the assay procedure is complete.

In an alternative device according to the invention, the detector reagent acts both to remove unbound sample and reagents from the detection zone and to facilitate analyte detection. Such a device may be designed essentially as shown in FIGS. 3 and 4, except that the device includes a single reagent storage vessel and a single reagent delivery wick (e.g., included as a component of the lance). As described above, sample is added to the device and, at some point after addition, the device is operator activated (as described above). The detector reagent storage vessel is pierced by the lance (containing a delivery wick) and the detector reagent delivered to the flow matrix. Reversal of the fluid flow (also as described above) draws the detector reagent into the flow matrix by capillary force. As the detector reagent flows towards the absorbent reservoir, it displaces the fluid in the flow matrix, clearing the matrix, and importantly, clearing the detection zone of unbound sample and unbound labeled specific binding reagent.

In the case of a labeled specific binding reagent conjugated to a radioactive, fluorescent, or light-absorbing molecule, the detector reagent acts merely as a wash solution facilitating detection of complex formation at the detection zone by washing away unbound labeled reagent.

In the case of a specific binding reagent conjugated, e.g., to an enzyme, the detector reagent includes, e.g., a substrate that produces a detectable signal upon reaction with the enzyme-antibody conjugate at the detection zone. In such a case, a finite quantity of inhibitor reagent may be incorporated into an inhibitor reagent pad located at the junction of the detector reagent delivery wick and the flow matrix or may be dried directly on to the flow matrix between the detector reagent delivery wick and the detection zone. When the finite quantity of inhibitor migrates out of the detection zone, detector reagent produces a detectable signal upon contact with the labeled specific binding reagent.

To ensure proper operation, any of the devices described herein may further include various binding reagents immobilized at the detection zone 20 at positions distinct from the analyte capture reagent(s). For example, an immunoreagent that recognizes the species-specific portion of a labeled specific binding reagent or the enzyme portion of an enzyme-labeled reagent may be included as a positive control to assess the viability of the reagents within the device. Additionally, a reagent, e.g., an antibody isolated from a non-immune member of the species from which the antibody portion of the immobilized capture reagent was derived may be included as a negative control to assess the specificity of immunocomplex formation. In one aspect of the invention, the detection zone material is avidin coated and is spotted or stripped with biotinylated capture reagents.

Optionally, any of the devices described herein may further include a soluble film 50 that separates the flow matrix 10 from the absorbent reservoir 38. Sample added to the flow matrix at the sample entry port 30 is thereby flowed in a single direction (i.e., away from the absorbent reservoir) maximizing the amount of sample that flows past the detection zone 20. The film is dissolved slowly by the fluid sample and, upon dissolution, contact occurs between the absorbent reservoir 38 and the flow matrix 10 and promotes a reversal of the fluid flow. A soluble film 52 may also be positioned between the liquid reagent storage vessels 40 and 44 and the flow matrix. Dissolution of the film by fluid from the liquid reagent storage vessels or sample that has flowed to the film allows delivery of the liquid reagents to the flow matrix. Reverse fluid flow draws the reagents into the matrix by capillary force.

The fundamental components of the invention may be packaged as a single unit or housed as several units for multiple-sample devices. Various packaging options in which liquid reagent storage reservoirs or sample entry points are shared between several flow matrix components may also be envisioned. In one particular example, the device contains multiple regions within the detection zone, each including a different analyte capture reagent (e.g., one may include an immobilized antibody specific for feline immunodeficiency virus and another may include an immobilized antibody specific for feline leukemia virus); a single biological sample (e.g., a sample of feline serum) is assayed for the presence of one or both viruses.

Preferably, the detection zone 20 is seen from the outside of the housing, allowing ready detection of assay results. The sample entry cup 30 is preferably designed such that the volume of the cup is at least as large as the total volume of sample required to perform the assay. In addition, the absorbent reservoir 38 is preferably of sufficient size to accommodate the total volume of sample as well as all added liquid reagents (i.e., detector reagent and wash reagent).

Although various specific embodiments of the present invention have been described herein, it is to be understood that the invention is not limited to those precise embodiments and that various changes or modifications can be affected therein by one skilled in the art without departing from the scope and spirit of the invention.

What is claimed is:

1. A device for conducting an assay to determine the presence or amount of an analyte in a fluid sample, the device comprising a flow path that facilitates fluidic flow by capillary action n, wherein the flow path comprises:
   (a) a first fluid permeable region for sample entry;
   (b) a second fluid permeable region;
   (c) a substantially fluid impermeable barrier comprising a hydrophobic spacer between the first and second regions; and
   (d) a fluidic bridge comprising a fluid permeable material overlapping at least a portion of each of the first region, the barrier and the second region, for providing fluid communication between the first and second regions, wherein the bridge further comprises a detection zone having an immobilized capture reagent.

2. The device of claim 1 wherein the first region, the second region and the barrier comprise a single piece of material and an area of the material comprising the barrier has been treated with a substance to render the area impermeable to liquid.

3. The device of claim 2 wherein the substance is a fluoro methacrylate polymer.

4. The device of claim 1 further comprising at least one of a sealed container containing a detector reagent and a sealed container containing a wash reagent.

5. The device according to claim 4 comprising at least one wick for introducing at least one of the wash reagent and the detector reagent from at least one sealed container such that at least one of the wash reagent and the detector reagent are transported by capillary flow to the fluid flow path.

6. The device according to claim 5 wherein the second region comprises at least one entry port for introducing at least one of the wash reagent and the detector reagent.

7. The device according to claim 4 wherein the first region comprises at least one exit port for the exit of the at least one of the wash reagent and the detector reagent.

8. The device according to claim 5 wherein the first region, the second region and the bridge are sized and positioned to cause the analyte to flow initially along the flow path in one direction from the first region toward and into the second region, and subsequently, upon introduction of the at least one of the wash reagent and the detector reagent into the flow path, the at least one of the wash reagent and the detector reagent flow along the flow path in a second direction opposite the first direction.

9. The device according to claim 1 wherein the immobilized capture reagent is selected from the group consisting of an antigen, antibody, ligand, receptor, nucleic acid molecule, and chemically reactive groups and fragments thereof.

10. A device for conducting an assay to determine the presence or amount of an analyte in a fluid sample, the device comprising a flow path that facilitates fluidic flow by capillary action, comprising:
  (a) a single piece of matrix material comprising a first fluid permeable region for sample entry; a second fluid permeable region; and a barrier that interrupts fluid communication between the first and second regions comprising an area of the matrix material that has been treated to render the area substantially impermeable to liquid, and
  (b) a fluidic bridge comprising a fluid permeable material overlapping at least a portion of each of the barrier, the first region, and the second region, wherein the bridge provides fluid communication between the first and second regions.

11. The device of claim 10 wherein the treatment of the matrix material comprises rendering the area impermeable to liquid with a fluoro methacrylate polymer.

12. The device of claim 10 wherein the fluidic bridge comprises a detection zone having an immobilized capture reagent.

13. The device according to claim 12 wherein the immobilized capture reagent is selected from the group consisting of an antigen, antibody, ligand, receptor, nucleic acid molecule, and chemically reactive groups and fragments thereof.

14. The device of claim 10 further comprising at least one of a sealed container containing a detector reagent and a sealed container containing a wash reagent.

15. The device of claim 14 further comprising at least one wick for introducing the at least one of the wash reagent and the detector reagent from the at least one sealed container such that the at least one of the wash reagent and the detector reagent are transported by capillary flow to the fluid flow path.

16. The device according to claim 14 wherein the second region comprises at least one entry port for introducing the at least one of the wash reagent and the detector reagent.

17. The device according to claim 14 wherein the first region comprises an exit port for the exit of the at least one of the wash reagent and the detector reagent.

18. The device according to claim 14 wherein the first region, the second region and the bridge are sized and positioned to cause the analyte to flow initially along the flow path in one direction from the first region toward and into the second region, and subsequently, upon introduction of the at least one of the wash reagent and the detector reagent into the flow path, the at least one of the wash reagent and the detector reagent flow along the flow path in a second direction opposite the first direction.

19. A kit for performing an assay for determining the presence or quantity of an analyte in a fluid sample by detecting the analyte or analogue bound to an immobilized capture reagent after unbound sample material has been washed away, the kit comprising a device according to claim 1, and a labeled specific binding reagent.

20. A kit for performing an assay for determining the presence or quantity of an analyte in a fluid sample by detecting the analyte or analogue bound to an immobilized capture reagent after unbound sample material has been washed away, the kit comprising a device according to claim 10, and a labeled specific binding reagent.

21. A method for producing a device for conducting an assay to determine the presence or amount of an analyte in a fluid sample, the device comprising a flow path that facilitates fluidic flow by capillary action,
  (a) providing a single piece of fluid permeable matrix material and creating a fluid impermeable barrier on the matrix material between a first region and a second region by treating the area with a substance to render the area substantially impermeable to fluid; and
  (b) securing a fluidic bridge comprising a fluid permeable material to the matrix material so that the bridge overlaps at least a portion of each of the
  (c) first region, the barrier and the second region, wherein the bridge provides fluid communication between the first and second regions.

22. The method of claim 21 wherein the substance is a fluoro methacrylate polymer.

23. The method of claim 21 further comprising providing a detection zone having an immobilized capture reagent on the fluidic bridge.

24. The method of claim 23 wherein the immobilized capture reagent is selected from the group consisting of an antigen, antibody, ligand, receptor, nucleic acid molecule, and chemically reactive groups and fragments thereof.

25. A device for conducting an assay to determine the presence or amount of an analyte in a fluid sample, the device comprising a flow path that facilitates fluidic flow by capillary action, comprising:
  (a) a single piece of hydrophobic matrix material that has been treated to have at least two fluid permeable regions separated by an untreated region that acts as a fluidic barrier between the at least two fluid permeable regions, and
  (b) a fluidic bridge comprising a fluid permeable material overlapping at least a portion of each of the at least two fluid permeable regions and the untreated region, wherein the bridge provides fluid communication between the at least two fluid permeable regions.

26. A device for conducting an assay to determine the presence or amount of an analyte in a fluid sample, the device comprising a flow path that facilitates fluidic flow by capillary action, wherein the flow path comprises:
  (a) a first fluid permeable region for sample entry;
  (b) a second fluid permeable region;
  (c) a substantially fluid impermeable barrier between the first and second regions; and
  (d) a fluidic bridge comprising a fluid permeable material overlapping at least a portion of each of the first region, the barrier and the second region, for providing fluid communication between the first and second regions, wherein the bridge further comprises a detection zone having an immobilized capture reagent;
wherein the first region, the second region and the barrier comprise a single piece of material and an area of the material comprising the barrier has been treated with a substance to render the area impermeable to liquid.

27. The device of claim 26 wherein the substance is a fluoro methacrylate polymer.

28. A kit for performing an assay for determining the presence or quantity of an analyte in a fluid sample by detecting the analyte or analogue bound to an immobilized capture reagent after unbound sample material has been washed away, the kit comprising a device according to claim 26, and a labeled specific binding reagent.

* * * * *